United States Patent [19]

Rogova et al.

[11] 4,015,981
[45] Apr. 5, 1977

[54] TOOTH FILLING ALLOY

[76] Inventors: Svetlana Tanovna Rogova, ulitsa Belomorskaya, 18, korpus 4, kv. 44; Mikhail Vladimirovich Pikunov, Vtoraya Parkovaya, 44, korpus 3, kv. 147; Alla Ivanovna Kuptsova, Slavyansky bulvar, 47, kv. 32; Galina Zakharovna Obukhova, Simferopolsky proezd, 16, korpus 2, kv. 82; Dmitry Mikhailovich Karalnik, Krasnoyarskaya ulitsa, 5, korpus 2, kv. 159; Anatoly Ivanovich Rybakov, ulitsa Bakinskikh komissarov, 3, korpus 1, kv. 84, all of Moscowcow, U.S.S.R.

[22] Filed: Mar. 30, 1976

[21] Appl. No.: 671,955

[52] U.S. Cl. .................... 75/134 B; 75/134 C; 75/134 T
[51] Int. Cl.$^2$ .................. C22C 30/02; C22C 30/04
[58] Field of Search ......... 75/134 R, 134 N, 134 B, 75/134 C, 134 T, 153, 154, 175 R, 175 A

[56] References Cited

UNITED STATES PATENTS 2,864,695  12/1958  Smith et al. .................... 75/154

FOREIGN PATENTS OR APPLICATIONS 293,602  1/1971  U.S.S.R.

OTHER PUBLICATIONS

Smith, D. L., et al.; *The Journal Of The American Dental Association* "Some Physical Properties of Gallium–Copper–Tin Alloys" vol. 53 No. 6, pp. 677–685; Dec., 1956.

*Primary Examiner*—L. Dewayne Rutledge
*Assistant Examiner*—Michael L. Lewis
*Attorney, Agent, or Firm*—Steinberg & Blake

[57] ABSTRACT

The alloy for filling tooth cavity contains the following elements, in per cent by weight: gallium, 36 – 40; tin, 26 – 27, and copper, 34 – 37. Said compound is prepared by mixing 40 – 45 per cent of a liquid gallium—tin alloy containing 11 per cent by weight of tin, with 55 – 60 per cent by weight of powdered copper-tin alloy ($Cu_3Sn$) having particle size not exceeding 40 microns. Said powder should contain particles sizing less than 20 microns in the quantity of 55–70 per cent by weight.

The proposed compound has both good elasticity and high strength; it is easily filled into the tooth cavity and can be readily shaped, and finally it can work in the mouth cavity for lengthy periods of time.

1 Claim, No Drawings

TOOTH FILLING ALLOY

This invention relates to stomatology and more particularly it relates to compounds used for filling tooth cavity.

Known in the prior art are various materials used for filling tooth cavities, e.g. silver amalgam, cements, and plastic materials. Silver amalgam, having good physical and mechanical properties is now widely used for filling molars, but owing to the presence of mercury in the amalgam (mercury vapour is harmful to man, especially to those engaged in the preparation of the amalgam) the necessity arises to provide new filling materials that would not be inferior to those on the basis of silver amalgam, but containing no mercury.

Known in the prior art are compounds containing gallium, or its alloys, together with nickel, cobalt, silicon, palladium, silver, and tin. These compounds are prepared by mixing gallium, or its alloys, with said elements in the powder form.

Known is a compound for filling tooth cavities containing 27 – 31 percent by weight of gallium, 29 – 30 percent by weight of tin and 40 – 43 percent by weight of copper (D. L. Smith, H. J. Caul, The Journal of the Americal Dental Association, 1956, vol. 53, No. 6, p. 677 – 695). The compound is prepared by mechanically mixing together 30 - 35 percent by weight of an eutectic gallium-tin alloy, containing 11 percent by weight, of tin, with 65 – 70 percent by weight of powdered copper-tin alloy ($Cu_3Sn$), having particles sizing maximum 40 microns (325 mesh). (The authors do not provide a detailed specification of the granulometric composition. The powder was obtained by grinding the alloy in an agate mortar).

D. L. Smith et al. have shown that compounds containing over 35 (e.g. 40) percent by weight of liquid gallium-tin alloy have low strength, while compounds containing 30 percent by weight of the liquid alloy become stiff and inapplicable for filling tooth cavity despite their high strength. In other words, it is impossible to increase elasticity of the compound by directly increasing the percentage of the liquid gallium-tin alloy since it drastically decreases the strength of the filling compound.

The above-cited authors propose that 3 compounds having the following composition (in percent by weight) should be used as filling materials;

| 1. Gallium | 31.0 | 2. Gallium | 29.0 | 3. Gallium | 27.0 |
|---|---|---|---|---|---|
| Tin | 29.0 | Tin | 29.0 | Tin | 30.0 |
| Copper | 40.0 | Copper | 42.0 | Copper | 43.0 |

The compression strength of said compounds is within the range of from 3010 to 3680 kg/sq.cm.

The authors propose that said compounds should be used for filling tooth cavity, but do not report or the results of the clinical tests.

As we tried the proposed compounds in clinic, we have found that they are insufficiently elastic and slowly set in the tooth cavity. In order to accelerate the setting process and also to increase elasticity of the compound, we used preheated tools, which added to the inconveniences. Our conclusion is that the above-proposed compounds cannot be widely used in stomatological practice.

The object of the present invention is to provide an improved compound containing gallium, tin, and copper, but having higher elasticity and high mechanical strength.

Said object has been attained by improving the compound for filling tooth on the basis of gallium-tin-copper alloys, having according to the invention, the following composition, in percent by weight:

| gallium | 36 – 40 |
|---|---|
| tin | 26 – 27 |
| copper | 34 – 37 |

Said composition, according to the invention, is prepared by mixing together 40–45 percent by weight of an eutectic liquid gallium-tin alloy (11 percent by weight of tin) with 55 – 60 percent by weight of powdered copper-tin alloy characterized by the formula $Cu_3Sn$, having particles sizing maximum 40 micron, and containing particles under 20 microns in the quantity of 55 – 70 percent by weight.

The proposed compound has an increased elasticity (as compared with the known compounds), and at the same time it possesses high physical and mechanical properties, including the compressive strength of 3840 kg/sq.cm. Owing to its high elasticity, the proposed compound can be easily filled into the tooth cavity and shaped to restore the anatomical form of the tooth without using any heated tools. The filling will adheres to the tooth cavity walls, quickly sets (ten minutes) and remains intact in the mouth cavity for prolonged time.

The obtained effect, namely, increased elasticity in combination with high strength, is quite unexpected. For if the gallium-tin alloy is added into the known compound in a quantity exceeding 35 percent by weight, the compound gains in elasticity but loses in strength. In the herein-proposed compound, despite the increased content of the gallium-tin alloy (namely 40 – 45 percent by weight) the high strength remains unaffected. This is explained by the fact that the proposed compound is prepared by using powdered copper-tin alloy characterized by the formula $Cu_3Sn$, having particles sizing not over 40 microns and containing the fraction of particles not exceeding 20 microns in size in the quantity of 55 – 70 percent by weight.

Thus, in the powdered alloy, copper-tin particles of small fractions predominate.

The high content of fine fractions is responsible for the high specific surface of the powder and correspondingly its high reactivity. This makes it possible to decrease the content of the powdered copper-tin alloy in the compound down to 55 – 65 percent by weight and to increase thereby the content of the gallium-tin alloy to 40–45 percent by weight.

Owing to the increased content of said liquid gallium-tin alloy the compound acquires higher elasticity without detriment to the strength, since the structure of the compound has changed due to the presence in it of the powdered copper-tin alloy $Cu_3Sn$ containing increased quantities of fractions sizing under 20 microns.

The above-listed advantages inherent in the herein-proposed compound can be attained with strictly observing the proposed method for its preparing.

Whenever the percent ratio of the liquid gallium-tin alloy to the powdered alloy $Cu_3Sn$ differs from the specified, or the granulometric composition of the $Cu_3Sn$ powder is different from the above specified standards, the compound will lack the desired properties.

To illustrate the dependence of the properties of the proposed compound on the composition and the method of its preparation, the following Table is given, in which the characteristics of similar known compounds are also given for the purpose of comparison.

The tabulated data show that the herein-proposed compound contains greater quantities of the liquid gallium-tin alloy and hence is more elastic. But this fact does not affect the strength of the compound. This, actually is the essence of the proposed invention.

Besides its direct application, the proposed compound can also be used as moulding material for preparing porcelain crowns.

It is known to use plastic materials, cements, and amalgam for the manufacture of shaped tooth patterns in orthopedic stomatology. The disadvantage inherent in plastic materials and cements is their shrinkage in the process of setting, which is detrimental to the accuracy in the preparation of porcelain crowns.

Table

| Composition, in per cent by weight | | | Content of particles sizing under 20 microns in $Cu_3Sn$ powder, % w/w* | Liquid to powder ratio, % w/w | Elasticity | Compression strength in 24 hours kg/cm² |
|---|---|---|---|---|---|---|
| Compound of the invention | Gallium | 40.0 | 57 | 45:55 | good | 3150 |
| | Tin | 26.0 | | | | |
| | Copper | 34.0 | | | | |
| | Gallium | 38.0 | 60 | 43:57 | good | 3450 |
| | Tin | 26.0 | | | | |
| | Copper | 36.0 | | | | |
| | Gallium | 36.0 | 68 | 40:60 | good | 3840 |
| | Tin | 27.0 | | | | |
| | Copper | 37.0 | | | | |
| Known compound | Gallium | 31.0 | 20** | 35:65 | low | 3010 (43,400 psi) |
| | Tin | 29.0 | | | | |
| | Copper | 40.0 | | | | |
| | Gallium | 29.0 | 20** | 33:67 | low | 3420 (49,300 psi) |
| | Tin | 29.0 | | | | |
| | Copper | 42.0 | | | | |
| | Gallium | 27.0 | 20** | 30:70 | low | 3680 (53,000 psi) |
| | Tin | 30.0 | | | | |
| | Copper | 43.0 | | | | |

Notes:
*Data obtained by sedimentation analysis of $Cu_3Sn$ powdered alloy
**Powders have been prepared by the method proposed by Smith et al.

Amalgam is therefore would be usually used for the purpose. But alongside with the positive properties (high strength, low shrinkage), amalgam has certain disadvantages: danger of work with mercury, and slow setting (the pattern can only be used for further work in 6 – 8 hours).

Using the proposed compound on the basis of gallium for preparing a pattern of a shaped tooth in the manufacture of porcelain crowns offers some advantages compared with amalgam. The material is more elastic and it better follows the contour of a shaped tooth; it sets quicker, and the pattern can already be used for further operations in 30 – 60 minutes. Insignificant volumetric changes in the proposed compound make it possible to prepare porcelain crown with a high accuracy.

For a better understanding of the invention, the following examples of its practical embodiment are given by way of illustration.

EXAMPLE 1 a. Preparing powdered copper-tin alloy $Cu_3Sn$

Copper-tin alloy $Cu_3SN$ is first ground in a crusher, and then finely disintegrated on a mill to reduce the alloy to particles sizing maximum 40 microns, the fraction of particles sizing less than 20 microns being 57 percent by weight.

b. Preparing the compound

An eutectic liquid gallium-tin alloy containing 11 percent by weight of tin (0.45 g) is loaded into a capsule and 0.55 g of powdered copper-tin alloy $Cu_3Sn$, obtained as set forth in para (a) is added. The liquid to powder ratio is 45:55. The capsule is placed in an amalgam mixer for twenty seconds. The resultant paste is removed from the capsule. The prepared compound has good elasticity. Its chemical composition, in percent by weight, is:

| | |
|---|---|
| gallium | 40.0 |
| tin | 26.0 |
| copper | 34.0 |

Physico-mechanical tests of the compound gave the following results:

the paste begins to lose its elasticity in 8 minutes;
the time in which the elasticity is lost completely, 35 min. compressive strength, in 24 hours, 3150 kg/sq.cm;
Brinell hardness, in 24 hours, 70 kg/sq.mm;
beding strength, in 24 hours, 870 kg/sq.cm
Impact strength, in 24 hours, 9.3 kg. cm/sq.cm

EXAMPLE 2

Powdered copper-tin alloy $Cu_3Sn$ is prepared by a procedure similar to that described in Example 1. The prepared powder has maximum particle size of 40 microns, the fraction containing particles sizing under 20 microns being 60 percent by weight. Liquid gallium-tin alloy is mixed with powdered copper-tin alloy in the ratio of 43:57. The obtained compound has good elasticity. Its chemical composition, in percent weight, is:

| | |
|---|---|
| gallium | 38.0 |
| tin | 26.0 |
| copper | 36.0 |

Physico-mechanical tests of the compound gave the following results:

the paste begins to lose its elasticity in 6 minutes; its loses the elasticity completely in 30 minutes; compressive strength in 24 hours is 3450 kg/sq.cm Brinell hardness in 24 hours, 79 kg/sq. mm bending strength in 24 hours, 955 kg/sq.cm impact strength in 24 hours, 10.4 kg.cm/sq.cm

EXAMPLE 3

Powdered copper-tin alloy $Cu_3Sn$ and the compound are prepared by the same procedure as described in Example 1. The obtained powdered copper-tin alloy has particles sizing maximum 40 microns, the fraction with particles sizing under 20 microns being 68 percent by weight. The liquid gallium-tin alloy is mixed with the powdered copper-tin alloy in the percentage ratio of 40 to 60. The obtained compound has good elasticity. Its chemical composition, in percent by weight, is:

| | |
|---|---|
| gallium | 36.0 |
| tin | 27.0 |
| copper | 37.0 |

The physico-mechanical properties of the compound are: the compound begins losing its elasticity in 5 minutes;

elasticity is lost in 25 minutes;

compressive strength in 24 hours, 3840 kg/sq.cm

Brinell hardness, 85 kg/sq.mm bedning strength in 24 hours, 1040 kg/sq.cm impact strength in 24 hours, 11.3 kg.cm/sq.cm The compound obtained in Example 2 was given toxicological and clinical trials.

It has been established that the quantities of gallium, tin and copper that can ingress the body in the corrosion of the filling in the mouth cavity, are small and cannot harm man. On the basis of these data, the results of studies on the action of the compound on soft animal tissues in subcutaneous a conclusion that the proposed compound is non-toxic.

We have observed hundred fillings in adults and two hundred fillings in children in the course of two years from the moment of tooth repare, and discovered the high clinical efficacy of the proposed compound. The compound well adheres the tooth walls, keeps the shapes, and does not affect the pulp. The compound proved especially effective in treating children with multiple caries.

We claim:

1. A tooth filling alloy having the following composition, in percent by weight:

| | |
|---|---|
| gallium | 36 – 40 |
| tin | 26 – 27 |
| copper | 34 – 37 | and prepared by mixing together 40 – 45 percent by weight of a eutectic liquid gallium-tin alloy containing 11 percent by weight of tin, with 55 – 60 percent by weight of a powdered copper-tin alloy of the formula $Cu_3Sn$, having particles of maximum size of 40 microns and containing 55 – 70 percent by weight of particles of $Cu_3Sn$ under 20 microns in size.

* * * * *